US006599535B2

(12) United States Patent
Guitard et al.

(10) Patent No.: US 6,599,535 B2
(45) Date of Patent: Jul. 29, 2003

(54) PHARMACEUTICAL COMPOSITIONS

(75) Inventors: Patrice Guitard, Hegenheim (FR);
Barbara Haeberlin, Riehen (CH);
Rainer Link, Staufen (DE); Friedrich Richter, Grenzach-Wyhlen (DE)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 10/194,826

(22) Filed: Jul. 12, 2002

(65) Prior Publication Data

US 2003/0008835 A1 Jan. 9, 2003

Related U.S. Application Data

(63) Continuation of application No. 09/725,733, filed on Nov. 29, 2000, now abandoned, which is a continuation of application No. 09/374,899, filed on Aug. 13, 1999, now Pat. No. 6,197,781, which is a continuation of application No. 08/981,952, filed as application No. PCT/EP96/03066 on Jul. 12, 1996, now Pat. No. 6,004,973.

(30) Foreign Application Priority Data

Jul. 14, 1995 (GB) .............................. 9514397
Jul. 21, 1995 (GB) .............................. 9515025

(51) Int. Cl.[7] ......................... A61K 9/14; A61K 31/44
(52) U.S. Cl. ...................... 424/489; 424/490; 424/493; 424/494; 424/497; 424/499; 424/501; 514/291; 514/297; 514/970
(58) Field of Search ............................ 424/489, 490, 424/493, 494, 497, 499, 501; 514/291, 297, 970

(56) References Cited

U.S. PATENT DOCUMENTS

| 3,852,421 A | 12/1974 | Koyanagi et al. | 424/94 |
|---|---|---|---|
| 3,929,992 A | 12/1975 | Sehgal et al. | 424/122 |
| 4,248,856 A | 2/1981 | Guley et al. | 424/21 |
| 4,309,404 A | 1/1982 | DeNeale et al. | 424/21 |
| 4,309,405 A | 1/1982 | Guley et al. | 424/21 |
| 4,415,547 A | 11/1983 | Yu et al. | 424/19 |
| 4,421,738 A | 12/1983 | Yamagiwa et al. | 424/35 |
| 4,650,666 A | 3/1987 | Izutsu et al. | 424/479 |
| 4,753,801 A | 6/1988 | Oren et al. | 424/465 |
| 4,916,138 A | 4/1990 | Ueda et al. | 514/294 |
| 5,026,560 A | 6/1991 | Makino et al. | 424/494 |
| 5,078,999 A | 1/1992 | Warner et al. | 424/501 |
| 5,100,883 A | 3/1992 | Schiehser | 514/183 |
| 5,100,899 A | 3/1992 | Calne | 514/291 |
| 5,145,684 A | 9/1992 | Liversidge et al. | 424/489 |
| 5,260,301 A | 11/1993 | Nakanishi et al. | 514/291 |
| 5,286,730 A | 2/1994 | Caufield et al. | 514/291 |
| 5,352,783 A | 10/1994 | Shafiee et al. | 540/456 |
| 5,384,130 A | 1/1995 | Kamada | 424/461 |
| 5,387,589 A | 2/1995 | Kulkarni | 514/291 |
| 5,456,923 A | 10/1995 | Nakamichi et al. | 424/489 |
| 5,457,111 A | 10/1995 | Luly et al. | 514/291 |
| 5,457,194 A | 10/1995 | Luly et al. | 540/456 |
| 5,472,954 A | 12/1995 | Loftsson | 514/58 |
| 5,514,686 A * | 5/1996 | Mochizuki et al. | 514/297 |
| 5,516,770 A | 5/1996 | Waranis et al. | 514/183 |
| 5,530,006 A | 6/1996 | Waranis et al. | 514/291 |
| 5,536,729 A | 7/1996 | Waranis et al. | 514/291 |
| 5,547,948 A | 8/1996 | Barcomb | 514/170 |
| 5,559,121 A | 9/1996 | Harrison et al. | 514/291 |
| 5,616,588 A | 4/1997 | Waranis et al. | 514/291 |
| 5,665,772 A | 9/1997 | Cottens et al. | 514/514 |

(List continued on next page.)

FOREIGN PATENT DOCUMENTS

| CA | 2164100 | 1/1995 |
|---|---|---|
| CA | 2170748 | 3/1995 |
| DE | 44 18 115 | 12/1994 |
| DE | 43 22 826 | 1/1995 |
| DE | 43 29 503 | 3/1995 |
| EP | 041 795 | 12/1981 |
| EP | 240 743 | 10/1987 |
| EP | 9240773 | 10/1987 |
| EP | 393 575 | 10/1990 |
| EP | 427 680 | 5/1991 |
| EP | 507 555 | 10/1992 |
| EP | 525 960 | 2/1993 |
| EP | 533 433 | 3/1993 |
| EP | 586 310 | 11/1993 |
| EP | 648 494 | 4/1995 |
| EP | 649 659 | 4/1995 |
| EP | 350 730 | 5/1995 |
| EP | 722 720 | 7/1996 |
| FR | 2 722 984 | 2/1996 |
| GB | 2278780 | 12/1994 |
| GB | 2279006 | 12/1994 |
| JP | 03-240726 | 10/1991 |
| WO | WO 91/16882 | 11/1991 |
| WO | WO 92/00739 | 1/1992 |
| WO | WO 92/02229 | 2/1992 |
| WO | WO 93/19763 | 10/1993 |
| WO | WO 96/14833 | 5/1996 |
| WO | WO 96/24332 | 8/1996 |
| WO | WO 96/25150 | 8/1996 |
| WO | WO 96/41807 | 12/1996 |
| WO | WO 97/02017 | 1/1997 |
| WO | WO 97/03654 | 2/1997 |

OTHER PUBLICATIONS

"Remington's Pharmaceutical Sciences", Fifteenth Edition, pp. 1422–1423, Mack Publishing Co. (1975).*
Derwent Abstract 94–033829/04 (TW 207954–A, Jun. 21, 1993).
Remingtons Pharmaceutical Sciences, 14th Edition, p. 1588 (1975).
Chiou et al., "Pharmaceutical Applications of Solid Dispersion Systems", J. Pharm. Sci., vol. 60, No. 9, pp. 1281–1302 (1971).
Ford, "The Current Status of Solid Dispersions", pharm. Acta. Helv., vol. 61, No. 3, pp. 68–88 (1986).

(List continued on next page.)

Primary Examiner—Frederick Krass
(74) Attorney, Agent, or Firm—John D. Thallemer

(57) ABSTRACT

A pharmaceutical composition in the form of a solid dispersion comprising a macrolide, e.g. a rapamycin or an ascomycin, and a carrier medium.

8 Claims, 1 Drawing Sheet

U.S. PATENT DOCUMENTS

| | | | |
|---|---|---|---|
| 5,686,110 A | 11/1997 | Greenwald et al. | 424/486 |
| 5,691,334 A | 11/1997 | Doria et al. | 514/235 |
| 5,725,883 A | 3/1998 | Staniforth et al. | 424/489 |
| 5,759,576 A | 6/1998 | Barcomb | 424/479 |
| 5,759,577 A | 6/1998 | Barcomb | 424/479 |
| 5,766,623 A | 6/1998 | Ayres et al. | 424/441 |
| 5,776,495 A | 7/1998 | Duclos et al. | 424/455 |
| 5,780,062 A | 7/1998 | Frank et al. | 424/501 |
| 5,817,333 A | 10/1998 | Kagayama et al. | 424/450 |
| 5,932,243 A | 8/1999 | Fricker et al. | 424/450 |
| 5,985,325 A | 11/1999 | Nagi | 424/482 |
| 5,989,591 A | 11/1999 | Nagi | 424/493 |
| 6,004,973 A | 12/1999 | Guitard et al. | 514/291 |
| 6,262,127 B1 | 7/2001 | Acemoglu et al. | 514/772 |

OTHER PUBLICATIONS

Approved Drug Products, 20th Edition, Prescription Drug Product List, pp. 3–311 (2000).

Derwent Abstract 96–335278 (EP722 720, Jul. 24, 1996).

Hahn et al., "Solid Surfactant Solutions of Active Ingredients in Sugar Esters", Pharm. Res., vol. 6, No. 11, pp. 958–960 (1989).

Serajuddin, "Solid Dispersion of Poorly Water–Soluble Drugs: Early Promises, Subsequent Problems, and Recent Breakthrough", J. Pharm. Sci., vol. 88, No. 10, pp. 1058–1066 (1999).

* cited by examiner

PHARMACEUTICAL COMPOSITIONS

This application is a continuation of 09/725,733, filed Nov. 29, 2000, now abandoned, which is a continuation of 09/374,899, filed Aug. 13, 1999, now U.S. Pat. No. 6,197,781, which is a continuation of 08/981,952, filed Jan. 26, 1998, now U.S. Pat. No. 6,004,973, which is a 371 of PCT Patent Application No. PCT/EP96/03066, filed Jul. 12, 1996, which in their entirety are herein incorporated by reference.

This invention relates to oral pharmaceutical compositions comprising a macrolide, e.g. a rapamycin or an ascomycin, in a solid dispersion.

Rapamycin is an immunosuppressive lactam macrolide produceable, for example by *Streptomyces hygroscopicus*. The structure of rapamycin is given in Kesseler, H., et al.; 1993; *Helv. Chim. Acta;* 76: 117. Rapamycin is an extremely potent immunosuppressant and has also been shown to have antitumor and antifungal activity. Its utility as a pharmaceutical, however, is restricted by its very low and variable bioavailability. Moreover, rapamycin is highly insoluble in aqueous media, e.g. water, making it difficult to formulate stable galenic compositions. Numerous derivatives of rapamycin are known. Certain 16-O-substituted rapamycins are disclosed in WO 94/02136, the contents of which are incorporated herein by reference. 40-O-substituted rapamycins are described in, e.g., in U.S. Pat. No. 5,258,389 and WO 94/09010 (O-aryl and O-alkyl rapamycins); WO 92/05179 (carboxylic acid esters), U.S. Pat. No. 5,118,677 (amide esters), U.S. Pat. No. 5,118,687 (carbamates), U.S. Pat. No. 5,100,883 (fluorinated esters), U.S. Pat. No. 5,151,413 (acetals), U.S. Pat. No. 5,120,842 (silyl ethers), WO 93/11130 (methylene rapamycin and derivatives), WO 94/02136 (methoxy derivatives), WO 94/02385 and WO 95/14023 (alkenyl derivatives) all of which are incorporated herein by reference. 32-O-dihydro or substituted rapamycin are described, e.g., in U.S. Pat. No. 5,256,790, incorporated herein by reference.

Further rapamycin derivatives are described in PC application number EP96/02441, for example 32-deoxorapamycin as described in Example 1, and 16-pent-2-ynyloxy-32(S)-dihydrorapamycin as described in Examples 2 and 3. The contents of PCT application number EP96/02441 are incorporated herein by reference.

Rapamycin and its structurally similar analogues and derivatives are termed collectively herein as "rapamycins".

On oral administration to humans, solid rapamycins, e.g. rapamycin, may not be absorbed to any significant extent into the bloodstream. Simple mixtures are known for rapamycins, e.g. rapamycin, with conventional pharmaceutical excipients; however, disadvantages encountered with these compositions include unpredictable dissolution rates, irregular bioavailability profiles, and instability. To date there is no conveniently administrable oral solid formulation available for rapamycin or a derivative thereof.

Accordingly, in one aspect, this invention provides a pharmaceutical composition in the form of a solid dispersion comprising a rapamycin and a carrier medium.

The compositions of this invention provide a high bioavailability of drug substance, are convenient to administer, and are stable.

Figure 1:
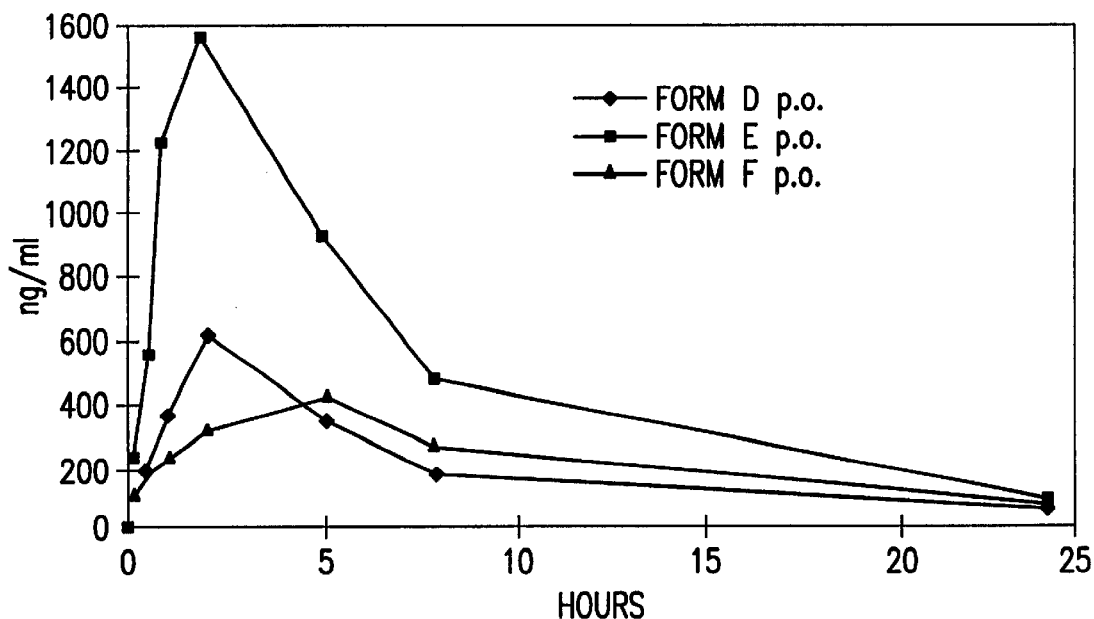
FIG. 1 is a plot of the mean blood levels of a formulation of 33-epichloro-33-desoxy-ascomycin without a surfactant and a formulation of 33-epichloro-33-desoxy-ascomycin with a surfactant.

The rapamycin used in the compositions of this invention may be any rapamycin or derivative thereof, for example as disclosed above or in the above-mentioned patent applications.

Thus the rapamycin used in the solid dispersion compositions of this invention may be rapamycin or an O-substituted derivative in which the hydroxyl group on the cyclohexyl ring of rapamycin is replaced by —OR$_1$ in which R$_1$ is hydroxyalkyl, hydroxyalkoxyalkyl, acylaminoalkyl and aminoalkyl; e.g. as described in WO94/09010, for example 40-O-(2-hydroxy)ethyl-rapamycin, 40-O-(3-hydroxy)propyl-rapamycin, 40-O-[2-(2-hydroxy)ethoxy]ethyl-rapamycin and 40-O-(2-acetaminoethyl)-rapamycin. The rapamycin derivative may be a 26- or 28-substituted derivative.

Preferred rapamycins for use in the solid dispersion compositions of this invention include rapamycin, 40-0-(2-hydroxy)ethyl rapamycin, 32-deoxorapamycin and 16-pent-2-ynyloxy-32(S)-dihydrorapamycin. A more preferred rapamycin is 40-0-(2-hydroxy)ethyl rapamycin (hereinafter referred to as compound X).

Numbering of rapamycin derivatives as used herein refers to the structure disclosed as Formula A at page 4 of published PCT application WO 96/13273, the contents of which are incorporated herein by reference.

The term solid dispersion as used herein is understood to mean a co-precipitate of the rapamycin, e.g. 40-0-(2-hydroxy)ethyl rapamycin or rapamycin, with the carrier medium. In the solid dispersion, the rapamycin is in amorphous or substantially amorphous form and is physically bound to the carrier medium.

Compositions of this invention may be administered in any convenient form, for example tablet, capsule, granule or powder form, e.g. in a sachet.

The rapamycin may be present in the composition in an amount of about 0.01 to about 30-weight-% based on the weight of the composition (% w/w), and preferably in an amount of 1 to 20% w/w based on the total weight of the composition.

The carrier medium is present in an amount of up to 99.99% by weight, for example 10 to 95 wt-%, based on the total weight of the composition.

In one embodiment the carrier medium comprises a water-soluble polymer, preferably a cellulose derivative such as hydroxypropylmethylcellulose (HPMC), hydroxypropylmethylcellulose phthalate, or polyvinylpyrrrolidone (PVP). Good results may be obtained using HPMC with a low apparent dynamic viscosity, e.g. below 100 cps as measured at 20° C. for a 2% by weight aqueous solution, e.g. below 50 cps, preferably below 20 cps, for example HPMC 3 cps. HPMC is well-known and described, for example, in the Handbook of Pharmaceutical Excipients, Second Edition, pub. Pharmaceutical Society of Great Britain and American Pharmaceutical Association, 1994, p.229 to 232, the contents of which are incorporated herein by reference. HPMC, including HPMC 3 cps, is available commercially under the trade name Pharmacoat 603 from the Shinetsu company.

PVP is available, for example, under the name Povidone (Handbook of Pharmaceutical Excipients), and a PVP having an average molecular weight between about 8,000 and about 50,000 Daltons is preferred.

In another embodiment the carrier medium comprises hydroxypropylcellulose (HPC) or a derivative thereof. Examples of HPC derivatives include those having low dynamic viscosity in aqueous media, e.g. water, e.g below about 400 cps, e.g below 150 cps as measured in a 2% aqueous solution at 25° C. Preferred HPC derivatives have a low degree of substitution, and an average molecular weight below about 200,000 Daltons, e.g. between 50,000 and 150,000 Daltons. Examples of HPC available commercially include Klucel L F, Klucel E F and Klucel J F from the Aqualon company; and Nisso HPC-L available from Nippon Soda Ltd;

a polyethylene glycol (PEG). Examples include PEGs having an average molecular weight between 1000 and 9000 Daltons, e.g. between about 1800 and 7000, for example PEG 2000, PEG 4000 or PEG 6000 (Handbook of Pharmaceutical Excipients);

a saturated polyglycolised glyceride, available for example under the trade mark Gelucir, e.g. Gelucir 44/14, 53/10, 50/13, 42/12, or 35/10 from the Gattefossé company; or a cyclodextrin, for example a β-cyclodextrin or an α-cyclodextrin. Examples of suitable β-cyclodextrins include methyl-β-cyclodextrin; dimethyl-β-cyclodextrin; hydroxypropyl-β-cyclodextrin; glycosyl-β-cyclodextrin; maltosyl-β-cyclodextrin; sulfo-β-cyclodextrin; sulfo-alylethers of β-cyclodextrin, e.g. sulfo-$C_{1-4}$-alkyl ethers. Examples of α-cyclodextrins include glucosyl-α-cyclodextrin and maltosyl-α-cyclodextrin.

The carrier medium may further comprise a water-soluble or water-insoluble saccharose or other acceptable carrier or filler such as lactose, or microcrystalline cellulose. The filler, if present, is generally in an amount of up to about 30% by weight, e.g. 0.5 to 20 wt-%, preferably, from about 5 to about 15% by weight of the composition. Microcrystalline cellulose is available commercially under the trade name Avicel, for example from FMC Corporation.

The carrier medium may further comprise one or more surfactants, for example a non-ionic, ionic, anionic or amphoteric surfactant. Examples of suitable surfactants include polyoxyethylene-polyoxypropylene co-polymers and block co-polymers known, for example, under the trade names Pluronic or Poloxamer, e.g. as described in Fiedler, H. P. "Lexikon der Hilfsstoffe für Pharmazie, Kosmetik und angrenzende Gebiete", Editio Cantor, D-7960 Aulendorf, 3rd revised and expanded edition (1989), the contents of which are hereby incorporated by reference. A preferred polyoxyethylene-polyoxypropylene block polymer is Poloxamer 188 available from the BASF company;

ethoxylated cholesterins known, for example, under the trade name Solulan, for example Solulan C24 commercially available from the Amerchol company;

vitamin derivatives, e.g. vitamin E derivatives such as tocopherol polyethylene glycol succinate (TPGS) available from the Eastman company;

sodium dodecylsulfate or sodium laurylsulfate;

a bile acid or salt thereof, for example cholic acid, glycolic acid or a salt, e.g. sodium cholate; or lecithin.

If present in the compositions of this invention, the surfactant(s) is generally in an amount of up to about 20%, for example 1 to 15% by weight.

One or more disintegrants may be included in the compositions of this invention. Examples of disintegrants include Polyplasdone (Handbook of Pharmaceutical Excipients) available commercially from the ISP company; sodium starch glycolate available commercially from the Generichem company; and crosscarmelose sodium available under the trade mark Ac-di-sol from FMC Corporation. One or more lubricants, for example magnesium stearate or colloidal silicon dioxide, may further be included in the composition of this invention in an amount of up to about 5 weight %, e.g. 0.5 to 2 wt-%, based on the weight of the composition.

It may be advantageous to include one or more flavouring agents in the compositions of this invention.

The present applicants have obtained good results using surfactant-free rapamycin compositions. In another aspect, therefore, this invention provides a surfactant-free solid dispersion composition comprising a rapamycin as described herein.

Antioxidants and/or stabilisers may be included in the compositions of this invention in an amount of up to about 1% by weight, for example between 0.05 and 0.5% by weight. Examples of antioxidants include butylated hydroxytoluene, DL-α-tocopherol, propyl gallate, ascobyl palmitate and fumaric acid. Malonic acid is an appropriate stabiliser.

In one embodiment of this invention, the composition comprises up to 30% by weight, e.g. 1 to 20 wt-%, 40-0-(2-hydroxy)ethyl rapamycin, and up to 95%, e.g. 30 to 90%, HPMC by weight.

The weight ratio of the rapamycin to carrier medium in the compositions of this invention is generally no more than 1:3, preferably less than 1:4.

In another aspect, this invention provides a process for preparing a solid dispersion composition as described herein.

In one embodiment the compositions of this invention may be obtained by dissolving or suspending the rapamycin and carrier medium in a solvent or solvent mixture. The solvent may be a single solvent or mixture of solvents, and the order of dissolution and suspension of the rapamycin with the carrier medium in the solvent may be varied. Solvents suitable for use in preparing solid dispersion compositions of this invention may be organic solvents such as an alcohol, for example methanol, ethanol, or isopropanol; an ester, e.g. ethylacetate; an ether, e.g. diethyl ether, a ketone, e.g. acetone; or a halogenated hydrocarbon, e.g. dichloroethane. A convenient solvent mixture is an ethanol/acetone mixture having a weight ratio of ethanol to acetone of between about 1:10 to about 10:1, for example 1:5 to 5:1.

Typically the rapamycin and carrier medium are present in a ratio by weight with the solvent of 1:0.1 to 1:20. The solvent may be evaporated and the rapamycin co-precipitated with carrier medium. The resulting residue may be dried, for example under reduced pressure, sieved and milled. The milled dispersion may be combined with other excipients and, for example, compressed as a tablet, or filled into sachets or gelatin capsules.

In another embodiment, the solid dispersion compositions may be prepared by melting the carrier medium to form a melt, and combining the melt with the rapamycin, e.g. by stirring, optionally in the presence of a solvent or solvent mixture as described herein.

Alternatively the solid dispersions of this invention may be prepared by spray drying techniques as described, for example, in Theory and Practice of Industrial Pharmacy, Lachmann et al., 1986. A suspension as formed above is dispersed through a nozzle into a chamber maintained at, for example, 20 to 80° C. The solvent is evaporated on passing through the nozzle, and finely dispersed particles are collected.

The compositions of this invention, after milling, typically have a mean particle size of less than about 0.5 mm, for example less than about 350 μm, e.g. about 100 to about 300 μm.

The oral compositions of this invention are useful for the known indications of the rapamycin, e.g. the following conditions:

a) Treatment and prevention of organ or tissue allo- or xeno-transplant rejection, e.g. for the treatment of recipients of e.g. heart, lung, combined heart-lung, liver, kidney, pancreatic, skin or corneal transplants. They are also indicated for the prevention of graft-versus-host disease, such as following bone marrow transplantation.

b) Treatment and prevention of autoimmune disease and of inflammatory conditions, in particular inflammatory conditions with an etiology including an autoimmune component such as arthritis (for example rheumatoid arthritis, arthritis chronica progrediente and arthritis deformans) and rheumatic diseases. Specific autoimmune diseases for which the compounds of the invention may be employed include, autoimmune hematological disorders (including e.g. hemolytic anaemia, aplastic anaemia, pure red cell anaemia and idiopathic thrombocytopenia), systemic lupus erythematosus, polychondritis, sclerodoma, Wegener granulamatosis, dermatomyositis, chronic active hepatitis, myasthenia gravis, psoriasis, Steven-Johnson syndrome, idiopathic sprue, autoimmune inflammatory bowel disease (including e.g. ulcerative colitis and Crohn's disease) endocrine ophthalmopathy, Graves disease, sarcoidosis, multiple sclerosis, primary billiary cirrhosis, juvenile diabetes (diabetes mellitus type I), uveitis (anterior and posterior), keratoconjunctivitis sicca and vernal keratoconjunctivitis, interstitial lung fibrosis, psoriatic arthritis, glomerulonephritis (with and without nephrotic syndrome, e.g. including idiopathic nephrotic syndrome or minimal change nephropathy) and juvenile dermatomyositis.

c) Treatment and prevention of asthma.

d) Treatment of multi-drug resistance (MDR). MDR is particularly problematic in cancer patients and AIDS patients who will not respond to conventional chemotherapy because the medication is pumped out of the cells by Pgp. The compositions are therefore useful for enhancing the efficacy of other chemotherapeutic agents in the treatment and control of multidrug resistant conditions such as multidrug resistant cancer or multidrug resistant AIDS.

e) Treatment of proliferative disorders, e.g. tumors, hyperproliferative skin disorder and the like.

f) Treatment of fungal infections.

g) Treatment and prevention of inflammation, especially in potentiating the action of steroids.

h) Treatment and prevention of infection, especially infection by pathogens having Mip or Mip-like factors.

i) Treatment of overdoses of FK-506 and other macrophilin binding immunosuppressants.

Where the pharmaceutical composition of this invention is in unit dosage form, e.g. as a tablet, capsule, granules or powder, each unit dosage will suitably contain between 1 mg and 100 mg of the drug substance, more preferably between 10 and 50 mg; for example 15, 20, 25, or 50 mg. Such unit dosage forms are suitable for administration 1 to 5 times daily depending upon the particular purpose of therapy, the phase of therapy and the like.

The exact amount of the compositions to be administered depends on several factors, for example the desired duration of treatment and the rate of release of the rapamycin.

The utility of the pharmaceutical compositions can be observed in standard clinical tests in, for example, known indications of active agent dosages giving equivalent blood levels of active agent; for example using dosages in the range of 1 mg to 1000 mg, e.g. 5 mg to 100 mg, of active agent per day for a 75 kilogram adult and in standard animal models. The increased bioavailability of the drug substance provided by the compositions can be observed in standard animal tests and in clinical trials.

The dosage form used, e.g. a tablet, may be coated, for example using an enteric coating. Suitable coatings may comprise cellulose acetate phthalate; hydroxypropylmethylcellulose phthalate; a polymethyacrylic acid copolymer, e.g. Eudragit L, S; or hydroxypropylmethylcellulose succinate.

The rapamycin used in the compositions of this invention, e.g. 40-0-(2-hydroxy)ethyl rapamycin or rapamycin, may be in crystalline or amorphous form prior to formation of the solid dispersion. An advantage, therefore, of this invention is that the rapamycin need not be crystalline. Thus the rapamycin may be used directly in combination, for example with a solvent, and does not have to be isolated in advance. Another advantage of the invention is that dissolution rates of the solid dispersion are higher than dissolution rates found for a crystalline rapamycin or an amorphous rapamycin in a simple mixture.

In another aspect, this invention provides a pharmaceutical composition in the form of a solid dispersion comprising an ascomycin and a carrier medium.

Examples of suitable ascomycins for use in the solid dispersion compositions of this invention include ascomycin or a derivative thereof, e.g. 33-epi-chloro-33-desoxy-ascomycin.

To date there is no conveniently administrable oral solid formulation available for 33-epi-chloro-33-desoxy-ascomycin. In another aspect, therefore, this invention provides a pharmaceutical composition in the form of a solid dispersion comprising 33-epi-chloro-33-desoxy-ascomycin and a carrier medium.

The compound 33-epi-chloro-33-desoxy-ascomycin is described in published European application EP 427 680 under Example 66a.

33-epi-chloro-33-desoxy-ascomycin will be referred to hereinafter as Compound Y.

The ascomycin, e.g. compound Y, compositions of this invention provide a high bioavailability of drug substance, are convenient to administer, and are stable.

The ascomycin, e.g. compound Y, may be present in the composition in an amount of about 0.01 to about 30% w/w, and preferably in an amount of 1 to 20% w/w.

The carrier medium may comprise any of the aforementioned components in amounts by wt-% as described above. Suitable water-soluble polymers, cyclodextrins and other excipients, e.g. surfactants, for use in the 33-epi-chloro-33-desoxy-ascomycin compositions of this invention are as described above.

In a preferred aspect, this invention provides a surfactant-containing composition comprising an ascomycin, e.g. compound Y, in the form of a solid dispersion as described herein.

The weight ratio of the ascomycin, e.g. compound Y. to carrier medium is generally no more than 1:3, preferably less than 1:4.

The ascomycin, e.g. compound Y, solid dispersion compositions may be prepared in analogous manner to the processes described above.

The oral compositions of compound Y disclosed herein are useful, for example, in the treatment of inflammatory and hyperproliferative skin diseases and of cutaneous manifestations of immunologically-mediated diseases. More specifically, the compositions of this invention are useful as antiinflammatory and as immunosuppressant and antiproliferative agents for use in the prevention and treatment of inflammatory conditions and of conditions requiring immunosuppression, such as a) the prevention and treatment of
   rejection of organ or tissue transplantation, e.g. of heart, kidney, liver, bone marrow and skin,
   graft-versus-host disease, such as following bone marrow grafts,
   autoimmune diseases such as rheumatoid arthritis, systemic lupus erythematosus, Hashimoto's thyroidis, multiple sclerosis, Myasthenia gravis, diabetes type I and uveitis,
   cutaneous manifestations of immunologically-mediated illnesses;
b) the treatment of inflammatory and hyperproliferative skin diseases, such as psoriasis, atopical dermatitis, contact dermatitis and further eczematous dermatitises, seborrhoeic dermatitis, Lichen planus, Pemphigus, bullous Pemphigoid, Epidermolysis bullosa, urticaria, angioedemas, vasculitides, erythemas, cutaneous eosinophilias, Lupus erythematosus and acne; and
c) Alopecia areata.

Where the pharmaceutical composition of this invention is in unit dosage form, e.g. as a tablet, capsule or powder, each unit dosage will suitably contain between 1 mg and 100 mg of the drug substance, more preferably between 10 and 50 mg; for example 15, 20, 25, or 50 mg. Such unit dosage forms are suitable for administration 1 to 5 times daily depending upon the particular purpose of therapy, the phase of therapy and the like.

In one embodiment of this invention, the composition comprises 30% by weight compound Y and 70% by weight HPMC in a dosage of e.g. 10 to 50 mg per day for use in, e.g. psoriasis, atopical dermatitis or contact dermatitis.

The exact amount of the compositions to be administered depends on several factors, for example the desired duration of treatment and the rate of release of compound Y.

The utility of the pharmaceutical compositions containing compound Y can be observed in standard clinical tests in, for example, known indications of active agent dosages giving equivalent blood levels of active agent; for example using dosages in the range of 1 mg to 1000 mg of active agent per day for a 75 kilogram adult and in standard animal models. The increased bioavailability of the drug substance provided by the compositions can be observed in standard animal tests and in clinical trials.

Following is a description by way of example only of solid dispersion compositions of this invention.

EXAMPLE 1

A solid dispersion composition is prepared containing the following ingredients (in parts by weight):

| | |
|---|---|
| Compound X | 9.1 |
| HPMC 3 cps | 81.8 |
| Lactose 200 mesh | 9.1 |

The composition (Form A) is prepared by dissolving the rapamycin and carrier medium in an ethanol/acetone mixture. Absolute ethanol is used in a 1:1 ratio by weight with the acetone. The solvents are then evaporated, and the resulting dry residue milled to a fine powder with mean particle size<0.5 mm.

EXAMPLE 2

A solid dispersion composition is prepared containing the following ingredients (in parts by weight):

| | |
|---|---|
| Compound X | 16.7 |
| HPMC 3 cps | 66.7 |
| Poloxamer 188 (from BASF) | 16.7 |

The composition (Form B) is prepared in analogous manner to that in Example 1.

EXAMPLE 3

A solid dispersion composition is prepared containing the following ingredients (in parts by weight):

| | |
|---|---|
| Compound X | 16.7 |
| HPMC 3 cps | 66.7 |
| TPGS* | 16.7 |

*tocopherol polyethylene glycol succinate

The composition (Form C) is prepared in analogous manner to that in Example 1.

EXAMPLE 4

A solid dispersion composition is prepared containing the following ingredients (in parts by weight):

| | |
|---|---|
| Compound X | 10 |
| HPMC 3 cps | 80 |
| Solulan C24 (from Amerchol) | 10 |

The composition (Form D) is prepared in analogous manner to that in Example 1.

The above compositions Forms A to D may be formed into tablets, filled into capsules, or powdered and packaged in sachets.

Pharmacokinetics After Administration of 40-O-(2-Hydroxy)Ethyl Rapamycin to Rats a) Drug Administration 0.5 ml aqueous dispersions of the Compound X compositions (corresponding to 4.0 mg active ingredient/rat) were administered by gastric intubation during a short inhalation anaesthesia with a 1 ml syringe, attached to a polyethylene tube. Six animals were used for each composition Forms A, B, C and D.

b) Blood Sampling

The animals received a permanent cannula into a vena jugularis one day prior to this experiment. 0.5 ml venous blood (vena jugularis) was collected from each rat and stored in 2.5 ml EDTA tubes. The blood samples of 2 animals (1 and 2, 3 and 4, 5 and 6) were pooled and stored at −80° C. until drug analysis. Samples were taken before administration and 10 minutes (m), 30 m, 60 m, 120 m, 300 m, 480 m and 1440 m after drug administration.

c) Bioanalytics

The blood samples were analysed using reversed phase HPLC.

Table 1 shows the pharmacokinetic data collected after administration of Compound X to rats.

TABLE 1

Summary Profiles (averages of 2–3 pools)

| time (h) | blood concentration (ng/ml) | | | |
|---|---|---|---|---|
| | Form A | Form B | Form C | Form D |
| 0 | 7 | 7 | 7 | 7 |
| 0.17 | 118 | 117 | 85 | 68 |
| 0.5 | 422 | 131 | 125 | 74 |
| 1 | 375 | 129 | 96 | 66 |
| 2 | 277 | 82 | 89 | 54 |
| 5 | 573 | 92 | 58 | 39 |
| 8 | 496 | 66 | 45 | 34 |
| 24 | 93 | 30 | 34 | 30 |
| Cmax (ng/ml) | 573 | 135 | 131 | 81 |
| Tmax (hr) | 5.00 | 0.50 | 0.50 | 0.50 |
| AUC 0–8 h [(ng/ml).h] | 3502 | 720 | 565 | 376 |
| AUC 0–24 h [(ng/ml).h] | 8213 | 1487 | 1192 | 886 |

Form A resulted in blood levels higher than those after administration of surfactant-containing compositions.

Dog Study

Following the above promising results, a relative bioavailability study was performed in fasted beagle dogs using a dose of 1 mg/kg body weight. Hard gelatin capsules each containing 10 mg compound X were administered to 8 dogs in a 4-way latin square design; the dogs were fed 6 hours post administration of the capsules, and blood levels of compound X were determined over 48 hours. Similar blood concentration profiles of compound X were observed for all the dogs, with a terminal halflife of compound X in blood between 10 and 40 hours. Median peak levels of 140 ng/ml and median AUC levels of 0–48 hr ca. 1600 ng.h/ml were observed.

EXAMPLE 5

A solid dispersion composition is prepared containing the following ingredients (in parts by weight):

| Compound Y | 20 |
|---|---|
| HPMC 3 cps | 80 |

The composition (Form E) is prepared by dissolving compound Y and carrier medium in an ethanol/acetone mixture. The solvents are then evaporated, and the resulting dry residue milled.

EXAMPLE 6

A solid dispersion composition is prepared containing the following ingredients (in parts by weight):

| Compound Y | 20 |
|---|---|
| HPMC 3 cps | 70 |
| Poloxamer 188 | 10 |

The composition (Form F) is prepared in analogous manner to that in Example 5.

EXAMPLE 7

A solid dispersion composition is prepared containing the following ingredients (in parts by weight):

| Compound Y | 20 |
|---|---|
| HPMC 3 cps | 75 |
| Sodium laurylsulfate | 5 |

The composition (Form G) is prepared in analogous manner to that in Example 5.

The above compositions Forms E to G may be formed into tablets, filled into capsules, or powdered and packaged in sachets.

Pharmacokinetics After Administration of 33-Epi-Chloro-33-Desoxy-Ascomycin to Rats a) Drug Administration 0.5 ml aqueous dispersions of the drug compositions (corresponding to 4.0 mg active ingredient/rat) were administered by gastric intubation during a short inhalation anaesthesia with a 1 ml syringe, attached to a polyethylene tube. Six animals were used for each composition Forms E, F, and G.

b) Blood Sampling

The animals received a permanent cannula into a vena jugularis one day prior to this experiment. 0.5 ml venous blood (vena jugularis) was collected from each rat and stored in 2.5 ml EDTA tubes. The blood samples of 2 animals (1 and 2, 3 and 4, 5 and 6) were pooled and stored at −80° C. until drug analysis. Samples were taken before administration and 10 minutes (m), 30 m, 60 m, 120 m, 300 m, 480 m and 1440 m after drug administration.

c) Bioanalytics

The blood samples were analysed using reversed phase HPLC.

Figure 2:
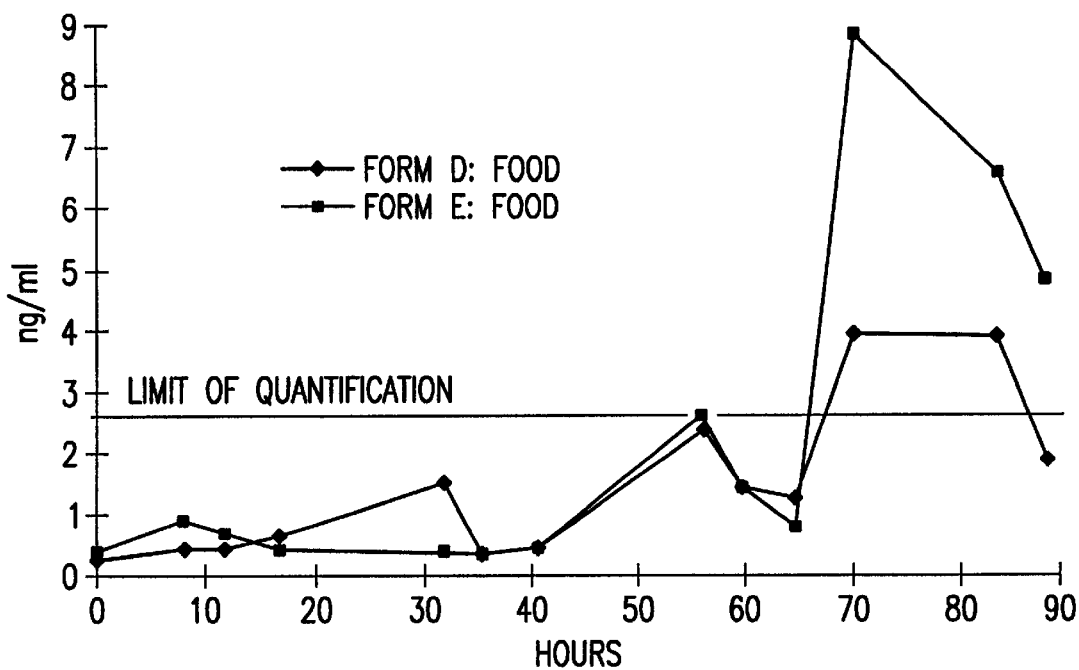
FIG. 2 is a plot of the blood levels of 33-epichloro-33-desoxy-ascomycin after in-food administration.

The results are plotted in FIGS. 1 and 2, in which ng/ml (vertical axis) is plotted against time in hours (horizontal axis).

FIG. 1 shows that Form F resulted in blood levels substantially higher than blood levels observed after administration of Form E or Form G.

FIG. 2 shows that Form F resulted in high blood levels when administered with food.

Compound Y is in amorphous form in the compositions E, F and G on formation and after 6 months storage as determined by X-ray diffraction.

Forms E, F and G are tested for respective dissolution rates. On stirring in a solution of 0.2 wt % sodium dodecylsulfate in water at 37° C., it is found that over 80% available compound Y is released and dissolved from each milled composition containing 10 mg compound Y after 30 minutes. 92% available compound Y is released from Form E. This compares with approximately 5% release after 30 minutes from an equivalent amount of crystalline compound Y.

What is claimed is:

1. A pharmaceutical composition in the form of a solid dispersion comprising 33-epichloro-33-desoxy-ascomycin and a carrier medium, wherein the pharmaceutical composition does not contain a surfactant.

2. The pharmaceutical composition according to claim 1 wherein the carrier medium comprises a water-soluble polymer or a cyclodextrin.

3. The pharmaceutical composition according to claim 2 wherein the water-soluble polymer is hydroxypropylmethylcellulose or polyvinylpyrrolidone.

4. The pharmaceutical composition according to claim 2 wherein the water-soluble polymer is present in an amount up to 95 weight percent, based on the total weight of the composition.

5. The pharmaceutical composition according to claim 1 wherein the ascomycin is present in an amount of up to 30 weight percent, based on the total weight of the composition.

6. The pharmaceutical composition according to claim 1 wherein the ascomycin is in amorphous form.

7. The pharmaceutical composition according to claim 1 which additionally comprises an antioxidant.

8. The pharmaceutical composition according to claim 7 wherein the antioxidant is selected from the group consisting of butylated hydroxytoluene, DL-α-tocopherol, propyl gallate, ascorbyl palmitate, fumaric acid, and combinations thereof.

* * * * *